US010765350B2

(12) United States Patent
Gupta et al.

(10) Patent No.: US 10,765,350 B2
(45) Date of Patent: *Sep. 8, 2020

(54) NONINVASIVE METHOD FOR ESTIMATING GLUCOSE BLOOD CONSTITUENTS

(71) Applicant: Analytics For Life, Ganaoque (CA)

(72) Inventors: Sunny Gupta, Amherstview (CA); Timothy Burton, Ottawa (CA); Matthew Howe-Patterson, Ottawa (CA)

(73) Assignee: ANALYTICS FOR LIFE INC., Toronto (CA)

( * ) Notice: Subject to any disclaimer, the term of this patent is extended or adjusted under 35 U.S.C. 154(b) by 293 days.

This patent is subject to a terminal disclaimer.

(21) Appl. No.: 15/460,341

(22) Filed: Mar. 16, 2017

(65) Prior Publication Data

US 2017/0181670 A1 Jun. 29, 2017

Related U.S. Application Data

(63) Continuation of application No. 14/596,541, filed on Jan. 14, 2015, now Pat. No. 9,597,021.

(60) Provisional application No. 61/927,457, filed on Jan. 14, 2014.

(51) Int. Cl.
*A61B 5/1455* (2006.01)
*A61B 5/145* (2006.01)
*A61B 5/00* (2006.01)

(52) U.S. Cl.
CPC .......... *A61B 5/1455* (2013.01); *A61B 5/0075* (2013.01); *A61B 5/14532* (2013.01); *A61B 5/14546* (2013.01); *A61B 5/681* (2013.01); *A61B 5/6898* (2013.01); *A61B 5/7246* (2013.01)

(58) Field of Classification Search
CPC .............. A61B 5/1455; A61B 5/14551; A61B 5/14552; A61B 5/14532; A61B 5/14546; A61B 5/681; A61B 5/6898; A61B 5/7246; A61B 5/0075
See application file for complete search history.

(56) References Cited

U.S. PATENT DOCUMENTS

| 5,068,536 | A | 11/1991 | Rosenthal | |
| 6,175,750 | B1 * | 1/2001 | Cook | G01J 3/28 600/310 |
| 2004/0152989 | A1 * | 8/2004 | Puttappa | A61B 5/14532 600/473 |
| 2005/0038332 | A1 * | 2/2005 | Saidara | A61B 5/0002 600/347 |
| 2006/0224058 | A1 | 10/2006 | Mannheimer | |

(Continued)

FOREIGN PATENT DOCUMENTS

WO 1993/007801 4/1993

*Primary Examiner* — Eric F Winakur
*Assistant Examiner* — Chu Chuan Liu
(74) *Attorney, Agent, or Firm* — Meunier Carlin & Curfman LLC

(57) ABSTRACT

A light-based method and technique for measuring the static and average plasma glucose concentration over a prolonged period of time. More specifically, the disclosure relates to a method that utilizes mathematical analysis of appendage mobile LED flash IR light transmittance, absorption and scattering by using high resolution mobile camera data to estimate the concentration of glucose and glycated hemoglobin (HbA1c) in millimoles per liter (mmol/L).

25 Claims, 8 Drawing Sheets

(56) References Cited

U.S. PATENT DOCUMENTS

| | | |
|---|---|---|
| 2008/0319286 A1 | 12/2008 | Ridder et al. |
| 2010/0268094 A1 | 10/2010 | Hasling et al. |
| 2011/0184295 A1 | 7/2011 | Orbach et al. |
| 2012/0078075 A1 | 3/2012 | Maynard et al. |
| 2013/0023742 A1 | 1/2013 | Molcho et al. |

\* cited by examiner

NONINVASIVE METHOD FOR ESTIMATING GLUCOSE BLOOD CONSTITUENTS

CROSS-REFERENCE TO RELATED APPLICATION

This application is a continuation of U.S. patent application Ser. No. 14/596,541, filed Jan. 14, 2015, and claims priority to U.S. Provisional Patent Application No. 61/927,457, filed Jan. 14, 2014, each entitled "NONINVASIVE METHOD FOR ESTIMATING GLUCOSE, GLYCOSYLATED HEMOGLOBIN AND OTHER BLOOD CONSTITUENTS," which are incorporated herein by reference in its entirety.

BACKGROUND

Diabetes mellitus is a widespread global epidemic threatening human health. Blood glucose self-monitoring is essential to prevent complications of diabetes in assessing normal glucose levels. Changes in diet, exercise and medications alters blood glucose in unpredictable ways, often requiring frequent skin punctures for traditional assessment of glucose levels. Effective glycemic monitoring and control is required in avoiding acute and chronic complications such as diabetic coma, protein glycation, crosslinking, microvascular disease and large vessel disease. A continuous non-invasive measure of blood glucose and glycated hemoglobin would provide diabetic patients with the information required to monitor and control the condition.

As shown in FIG. 1, glycated hemoglobin (HbA1c) may be an indicator of diabetes risk. It has been found to be a better indicator than the commonly used measure of fasting glucose. Recent research by the Johns Hopkins Bloomberg School of Public Health has suggested that measurements of HbA1c more accurately identify individuals at risk of diabetes than the commonly used measurement of fasting glucose. The HbA1c test has low variability on a daily basis and levels are not as affected by illness and stress. It is a more stable marker of mean blood glucose over three months and as such the patient does not need to fast prior to the test being performed.

Optical devices such as near-infrared spectroscopy (NIRS) for the measurement of blood characteristics have been used in many areas of blood and tissue constituent diagnosis, cholesterol levels, liver enzymes (aspartate transaminase and alanine transaminase), bilirubin levels, lactic acid levels, blood oxygen saturation, glucose, hemoglobin, glycated hemoglobin and others. Different blood constituents have varying optical properties depending on conjugation, chirality, molecular weight and electron cloud topology. These optical properties can be used to identify the IR spectral signature of soft tissue absorption, transmittance and scattering in a blood constituent of interest. An example of this is shown in FIG. 10 where a comparison of IR absorption spectra is shown for glycated (HbA1c) and normal hemoglobin (Hb). Various blood constituents require the use of specialized light frequencies to maximize absorption in order to detect light intensity which often directly correlates to concentration and osmolarity. These specialized light frequencies require the use of narrow band infrared light sources such as infrared light emitting diodes (IR LEDs), or index and gain guided lasers and its compliment detector pairs (IR sensitive photo transistor).

A particularly well-known technique for the measurement of blood characteristics is pulse oximetry. A pulse oximetry device, such as shown in FIG. 2, measures the oxygen saturation of blood. Pulse oximetry involves the transmission of two or more wavelengths of infrared (IR) light where blood perfuses the tissue, for example at a finger or earlobe. An IR LED is the most common source of the light used in pulse oximetry. A photodetector, such as a photodiode or a photo transistor, senses the absorption and transmittance of light from the other side of the tissue.

Simple phototransistors can only sense absorption and transmittance of light. To enhance IR spectral content and its intensity spatial properties, integrated mobile cameras and LED flashes can be used to extract blood absorption, scattering and transmittance IR spectra intensity matrix data.

SUMMARY OF THE DISCLOSURE

The disclosure generally relates to a noninvasive light-based method and technique for measuring the static and average plasma glucose concentration over a prolonged period of time. More specifically, the disclosure relates to a method that utilizes mathematical analysis of appendage mobile LED flash IR light transmittance, absorption and scattering by using high resolution mobile camera data to estimate the concentration of glucose and glycated hemoglobin (HbA1c) in millimoles per liter (mmol/L).

In accordance with some implementations, there is provided a method of performing light-based tissue perfusion blood constituent analysis, using a device having an objective lens and an external light source. The method includes placing the device such that the objective lens is completely obstructed; covering the external light source by at least part of a soft tissue appendage by placing the appendage against a frame of the objective lens while continuously illuminated by the external light source; operating a video recording device to capture the digital signature of absorbed, transmitted and scattered light from the soft tissue appendage; and analyzing signals from the video recording device to determine information about blood constituents in the appendage.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
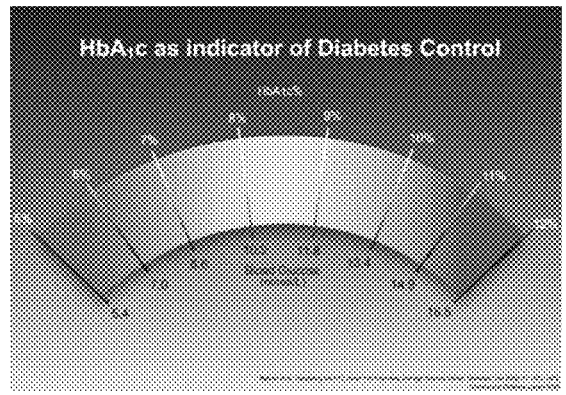
FIG. 1 shows a diagram of hemoglobin A1c as an indicator of diabetes risk over a range of values from 5.4 to 16.5 mmoles/litre.
Figure 2:
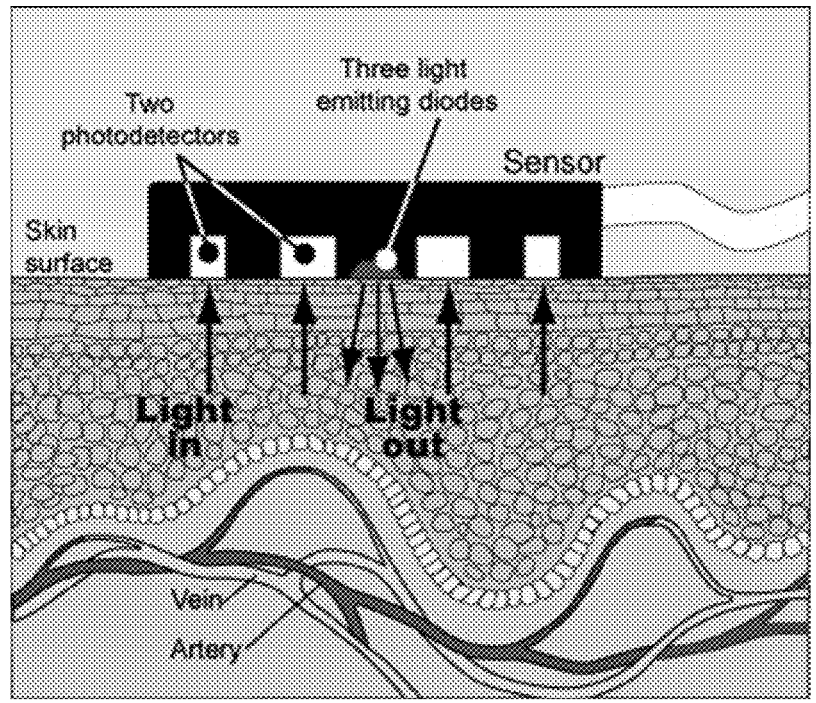
FIG. 2 illustrates a commercial pulse oximetry device showing soft tissue and an emitter detector array.
Figure 3:
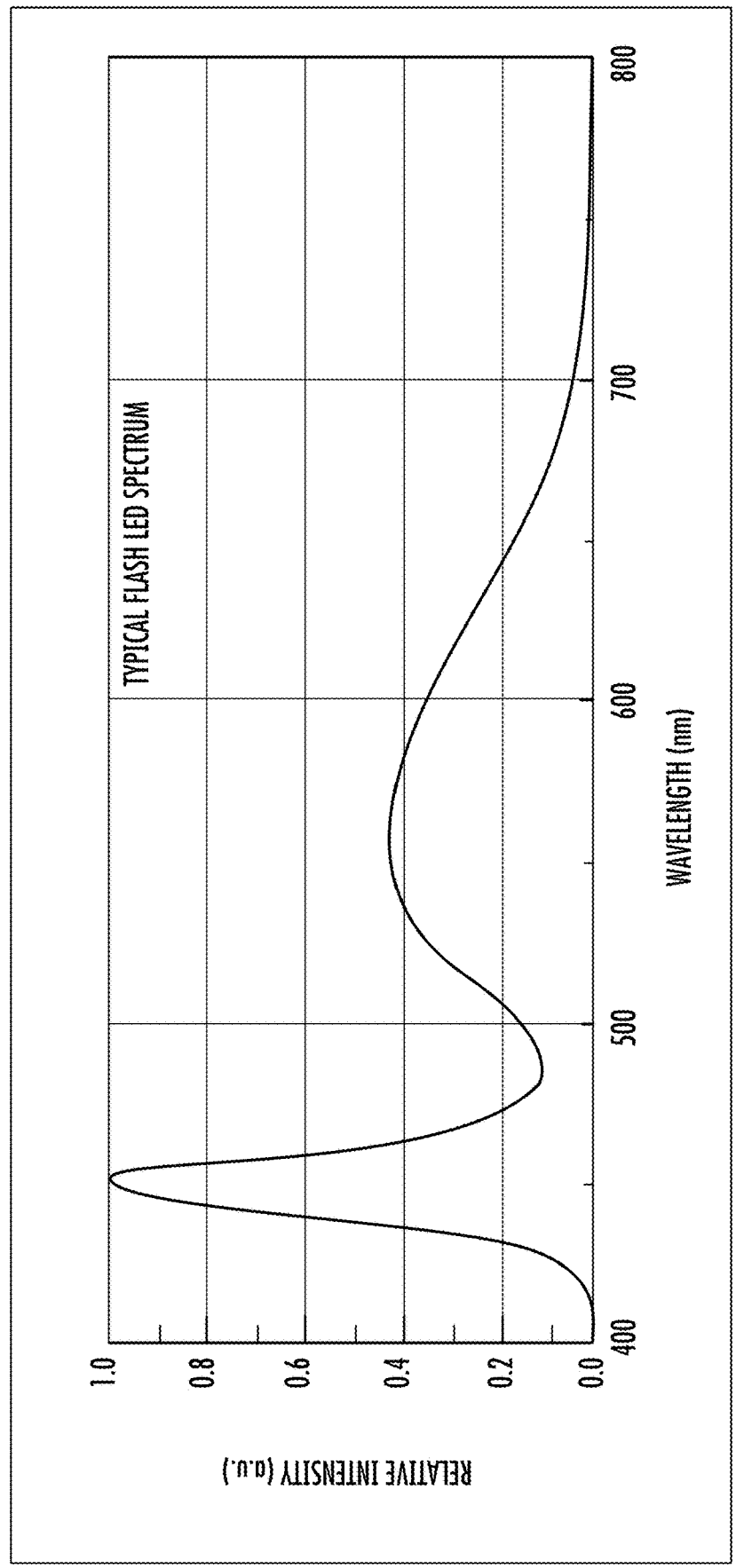
FIG. 3 illustrates a typical flash LED spectrum.

The present disclosure provides a method of performing blood and tissue constituent analysis using a mobile video camera, which includes an objective lens and a simple LED flash light source. The disclosure provides a mathematical method of extracting concentration of glucose and glycated hemoglobin and other blood constitutes from soft tissue perfusion videos (20 seconds to 5 minutes in length) of light absorbed, transmitted and scattered by the adjacent flash LEDs commonly used in mobile phone/watch cameras or other such portable devices. Most if not all blood and tissue constituents are optically active in the near-infrared range (NIR) range. A significant feature of this disclosure and unique art is to analyze the native IR filtered complementary metal-oxide semiconductor (CMOS) camera perfusion videos, in the presence of a non-ideal spectrally stochastic white flash LED light source (FIG. 3), and correlating these data to blood and tissue constituents.

The method comprises placing the video camera's objective lens and LED flash so both are completely obstructed by direct contact with soft tissue, which is a component of an individual's appendage with active cutaneous blood flow. The appendage can be any soft tissue which light can pass without obstruction of body hair and minimal underlying high-density structures. An example of this is a fingertip, which has hairless soft tissue surrounding the phalanges and has minimal bone mass. The appendage is placed firmly against the frame of the objective lens or against a restricting frame that obstructs part of the objective lens. The method does not require a focused image of the appendage. The video camera records for a short period of time while the LED is simultaneously active, typically 20 seconds to 5 minutes. The resulting video data is characterized by analyzing spatial spectral and non-Fourier CMOS signals from the video camera to monitor absorption, transmittance and scattering. This embodiment is referred to as a perfusion video which is a digital video made up of CMOS images collected at 15 to 120 frames per second of the LED illumination of appendage tissue used to determine blood glucose levels. The changes in spatial phase space and spectral correlations are used to deduce information on the blood and tissue constituent analysis in the appendage.

The process for transforming the video data to maximize informativeness and then linking the transformed data to levels of glycated hemoglobin and other blood constituents lies at the core of the disclosure. At each frame of the acquired video, the time averaged power spectral density (PSD) of the light entering the camera and striking each pixel is represented by a triplet of intensity values where each member of the triplet ranges from 0 to 255. These values are derived from three individual sensors, each with filters optimized to detect red light (wavelength of 620-750 nanometers), green light (wavelength of 495-570 nanometers) or blue light (wavelength of 450-495 nanometers). These filters however, will be redundant as the high intensity of the IR absorption, scatter and transmittance characteristics of various blood constituents, such as, e.g., HbA1c will bleed past the color filters. Even though a single frame of video contains in the order of millions of pixels, the process herein will illustrate the generalization to a single pixel in a given frame, or triplet value. This formulation can be extended to a spatial average over many pixels in a region of a frame, a time average of a region of pixels over successive frames, or any other expansion using more complex signal processing techniques. RBG values are unsuitable for direct use in spectral analysis, as the three numerical members do not contain sufficient information to reconstruct the entire PSD with sufficient fidelity. However, it is not necessary to reconstruct the entire PSD for accurate prediction of glycolated hemoglobin levels since the PSD for high levels of glycolation and low levels of glycolation are known. The PSD of other blood constituents are also known and follow the same process.

To approximately reconstruct the PSD, the following three equations determine the RGB values from a given PSD, with the knowledge that the light has first passed through a broadband red, green or blue filter, respectively, before encountering the sensor.

$$R = \int_0^\infty d\lambda (T_R(\lambda) I(\lambda)) \quad [1]$$

$$G = \int_0^\infty d\lambda (T_G(\lambda) I(\lambda)) \quad [2]$$

$$B = \int_0^\infty d\lambda (T_B(\lambda) I(\lambda)) \quad [3]$$

where $\lambda$ denotes the wavelength of the electromagnetic energy, $T(\lambda)$ is the transmittance function of the respective filter and $I(\lambda)$ denotes the intensity of the light at a given wavelength in the incident beam, which is henceforth referred to as the intensity function. The three transmittance functions may be determined experimentally, or may be provided by the camera manufacturer. A candidate intensity function can be constructed, parameterized by three values (generically named a, b, and c) such that for some values of the parameters the candidate intensity function sufficiently matches the intensity function for glycolated hemoglobin, or whichever blood constituent is under examination, then equations 1-3 form an invertible system of equations. The solution to this invertible system of equations forms an approximation of the generating intensity function. The parameterization should also be chosen as to continuously span the space of intensity functions between the two extremes. In one instance of the claimed invention, these parameterizations are used because they are more useful metrics than RBG values for determining levels of glycated hemoglobin and other blood constituents. This is due to the incorporation of some prior knowledge of the physics and signal processing of the camera system, as well as the PSD of blood constituents at various concentrations. A time series of the estimated PSDs can then be constructed using the methods mentioned above as the next step for linkage between video data and levels of blood constituents.

The video data transformed to a time series of estimated PSDs can then be analyzed one or both of two main processes: model based and signal density based. Model based analysis transforms the PSD time series to a noiseless model using modified matching pursuit (MMP). Signal density based segregates the signal into subspaces, which are then quantified. Signal density based analysis can be applied to the MMP model, or alternatively to the PSD time series itself. Subspace extraction analysis is applied to the MMP model.

Figure 4:
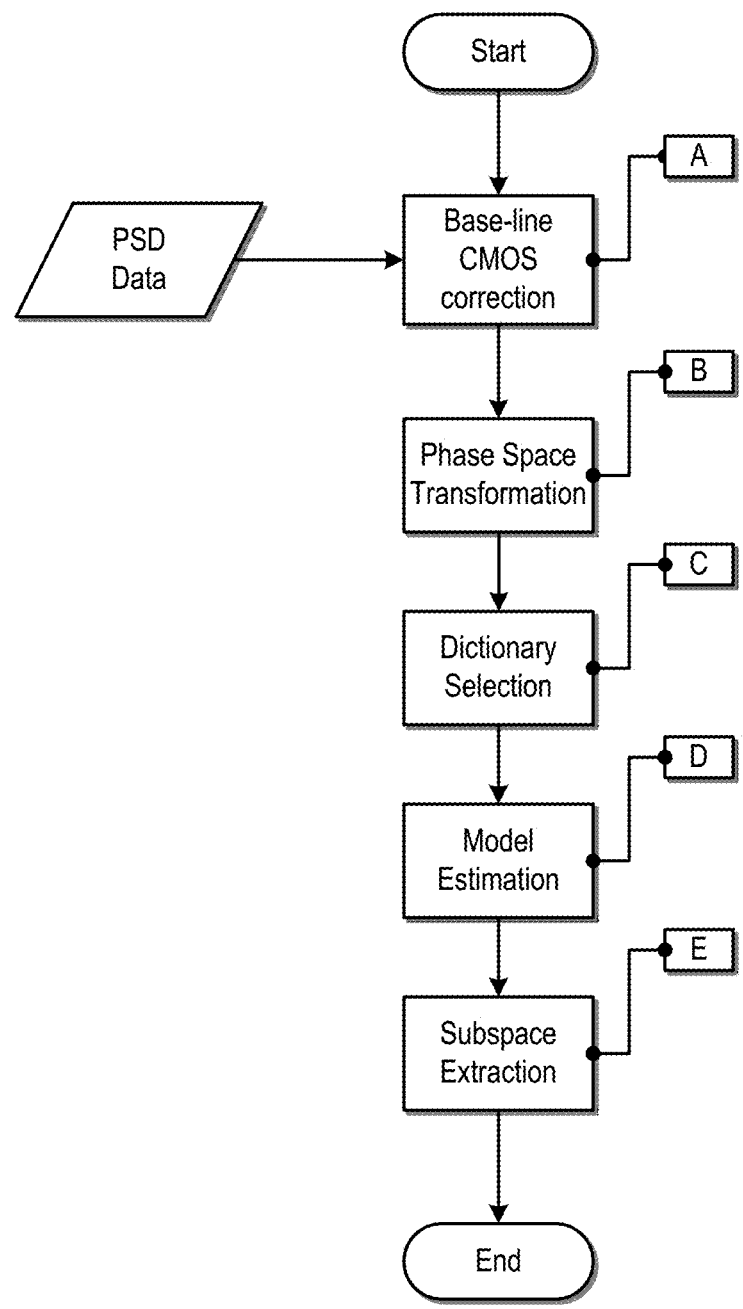
FIG. 4 illustrates the steps of the model based analysis to derive a noiseless sparse model from the power spectral density (PSD) time series data using an MMP algorithm.
Figure 5:
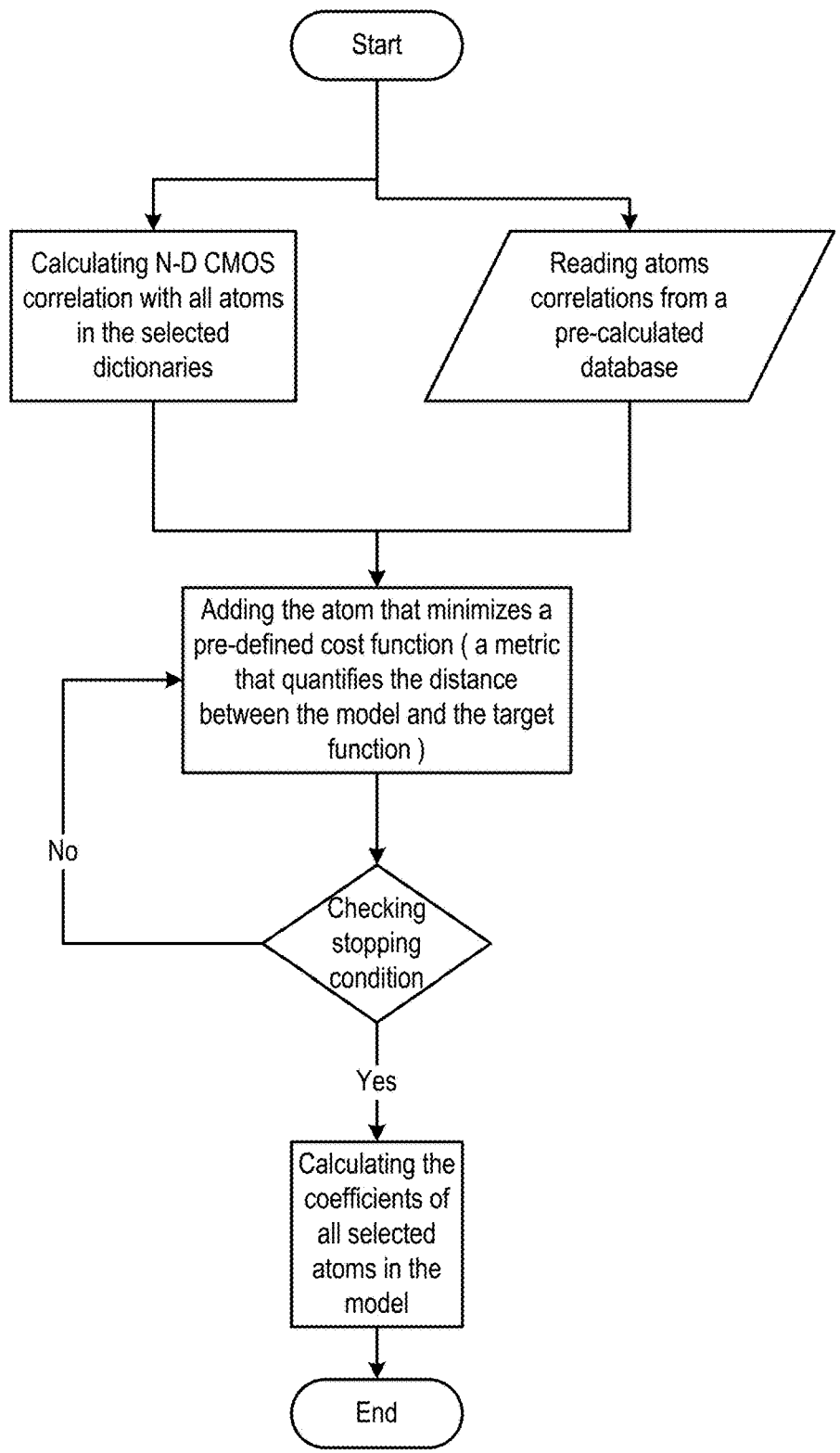
FIG. 5 is a visualization of the model estimation of FIG. 4.

FIG. 4 illustrates the steps of the model based analysis to derive a noiseless sparse model from the PSD time series data using an MMP algorithm. Firstly, baseline line CMOS correction (A) is designed to normalize and compensate for differences in relative intensity between the RGB PSD matrix. Triplet values form a 3D phase space. The signal is then decomposed using candidate functions selected from the most suitable dictionary(ies). Each dictionary D is a family of waveforms $D=(\phi_i | i \in I)$, of which there are many possible choices such as Wavelet Packets, Cosine Packets, Chirplets, and so on. Waveforms are selected iteratively from the dictionary based on pre-computed cross correlation with the target signal as well as a pre-defined cost function. Once selected, the waveform is subtracted from the signal to deduct complexity. Terms continue to be selected from the chosen dictionary until a predetermined stopping condition is satisfied. There are many ways of defining the stopping condition, and could be composed of the following exemplar metrics: mean squared error, number of terms selected, correlation between the signal and the model. Once the stopping condition is fulfilled, then the coefficients of the chosen candidate functions are calculated. The model estimation steps are shown in FIG. 5.

Once the MMP model has been computed from the PSD time series then different informative subspaces are extracted from it. These subspaces may include, but are not limited to complex sub harmonic frequency (CSF) trajectory, quasi-periodic and chaotic subspaces, low/high energy subspaces, and fractional derivatives of the low/high energy subspaces. These subspaces are exemplars of the family of subspaces that characterize the dynamics of the system, whether pathological or normal.

The signal density analysis previously mentioned can be applied to the PSD time series or the MMP modeled PSD time series. The signal density analysis involves segmenting the space-time domain into a number of regions, which total at least 12, from the center of gravity and the density of each segment is calculated. The density values contain specific information about non-linear variability of the PSD over time that contains information related in a complex manner to levels of blood constituents.

Figure 6:
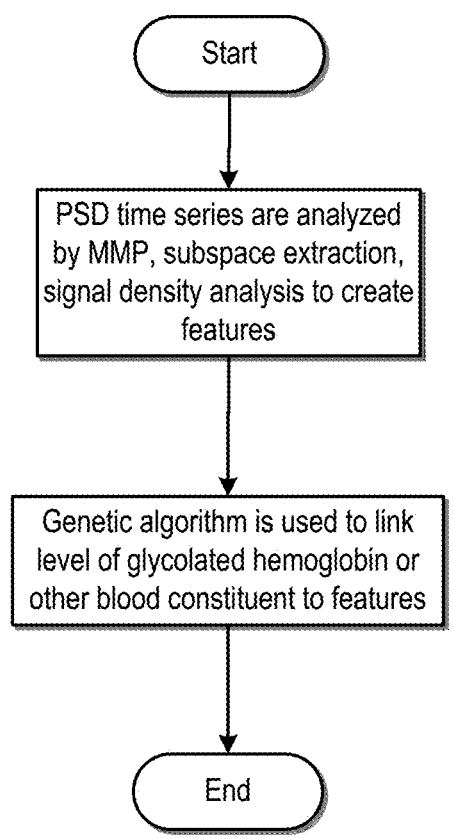
FIG. 6 is an overview of the feature extraction from the PSD time series.

The overview of the feature extraction from the PSD time series is shown in FIG. 6. In one implementation of the disclosure, the PSD time series progresses directly to signal density analysis. In another implementation, the PSD time series also progresses to MMP modeling and subsequently to subspace extraction. Quantifications of the dynamics of the system can be extracted at several points during this process.

Genetic algorithms are members of the class of evolutionary algorithms, which generate solutions to optimization problems using techniques inspired by evolution on a cellular scale as well as population scale. Solutions to the optimization problem can be viewed as genetic code. On a cellular scale, alterations in the genetic code can occur via the mutation and crossover operations, where mutation stochastically changes the potential solution and crossover combines two potential solutions. On a population level, solutions are viewed as individuals. Individuals are allowed to propagate through generations when they are well adapted to the problem. The level of adaptation of any given solution is measured by the fitness function, which compares the target attribute to the output of the equation through mean square error, mean absolute error, correlation coefficient, or any number of other metrics. The features summarized above become terms in the equation, which is the individual in the evolutionary paradigm. These terms in the equation are combined using many linear and nonlinear functions such as product, division, addition, subtraction, sin, cos, tan, tan h, cos h, sin h, gaussian, integral of the gaussian, exponential and logistic. A set of equations, of size 20 for example, form a population. As the population evolves and traverses the solution space, its members begin to converge with respect to similarity of solution and fitness function evaluation as they approach a maximum in the space, which is not necessarily the global maximum.

Figure 7:
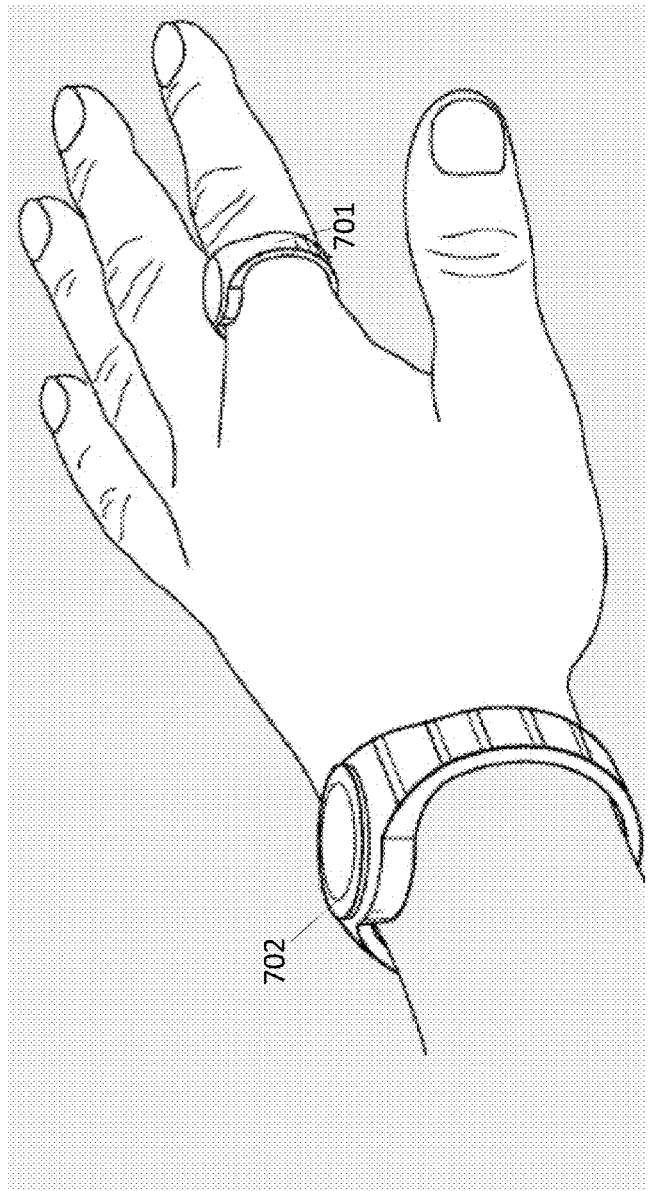
FIG. 7 illustrates an example implementation of a device to measure concentrations of glucose and glycated hemoglobin and other blood constituents using a light source.

FIG. 7 illustrates an example implementation of a device to measure concentrations of glucose and glycated hemoglobin and other blood constituents using an external light source. For example, a ring containing a CMOS array and laser diode may be placed on a subject's finger or smartwatch. Remote receiver (smart watch or mobile phone) 702 may receive information from the ring 701 and process the information using wireless low energy Bluetooth, as described below with reference to FIG. 8. Other implementations may be used, for example the CMOS array and laser diode may be integrated into the remote receiver 702, or the CMOS array and laser diode may be contained in a device that is located elsewhere on the subject's body in an area of soft tissue.

Figure 8:
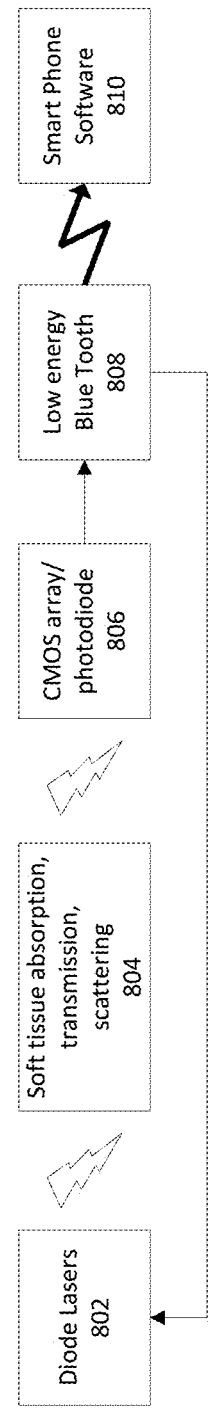
FIG. 8 illustrates an example high-level operational flow of the processes performed to determine concentrations of glucose and glycated hemoglobin and other blood constituents using a light source.

FIG. 8 illustrates an example high-level operational flow of the processes performed to determine concentrations of glucose and glycated hemoglobin and other blood constituents using an external light source. At 802, diode laser activated to illuminate the soft tissue area of the subject. At 804, soft tissue absorption, transmission and scattering is measured using, e.g., a CMOS array/laser diode (at 806). At 808, information received by the CMOS array/laser diode transmitted by, e.g. a low-energy Bluetooth connection (808) to a remote source (810), such as a smartphone running software that is adapted to process information received by the CMOS array/laser diode. The CMOS array/laser diode could be integrated into a smartwatch (702) and/or ring (701) and connected to smartphone via Bluetooth. Multiple frequencies of laser light could be used to detect varies blood constituents.

Figure 9:
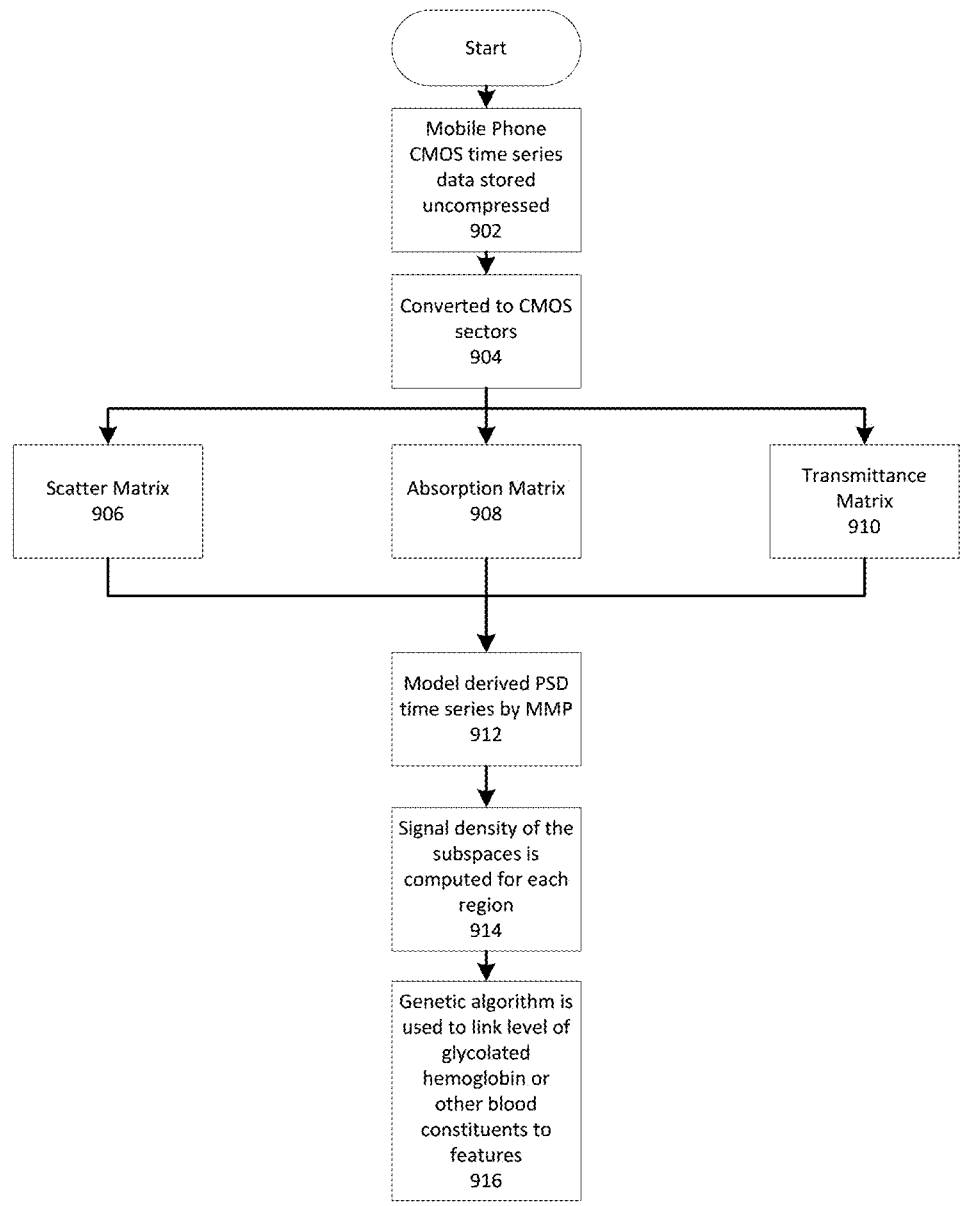
FIG. 9 illustrates a process for creating an equation linking PSD time series to level of glycolated hemoglobin or other blood constituents.
Figure 10:
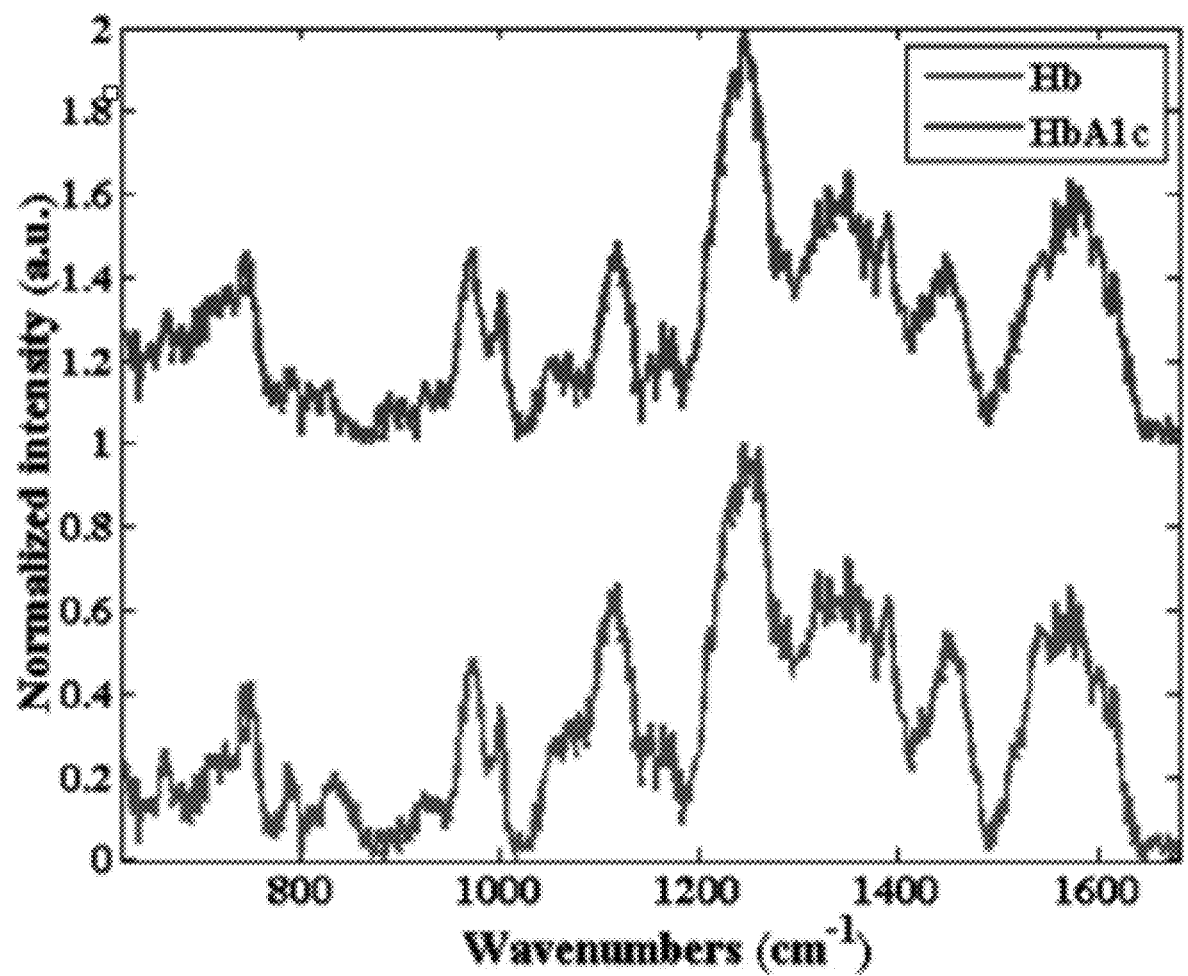
FIG. 10 illustrates the difference between the normalized Hb and HbA1c spectra.

The process for creating an equation linking PSD time series to levels of glycated hemoglobin or other blood constituents is described in FIG. 9. The features are extracted from a database of perfusion videos, which have associated blood panels. The genetic algorithm is then employed to create an equation that models levels of blood constituents as a function of the features.

A smart phone camera or smart watch camera is the ideal embodiment if the color CMOS camera is 8 megapixels or higher resolution. Mobile phone software can used to create perfusion videos (20 seconds to 5 minutes in length) of light absorbed, transmitted and scattered by the adjacent LED flash. Videos can be sent wirelessly to cloud computers for processing levels of blood glucose, glycated hemoglobin and other blood constituents. This information may be stored as uncompressed time series data at 902.

At 904, time series data is converted to CMOS sectors. The CMOS sectors from 904 are placed into matrices—a scatter matrix 906, an absorption matrix 908, and a transmittance matrix 910. At 912, MMP techniques may be used to model the PSD time series, which may be model based and/or signal density based. At 914, the signal density based model segregates the signal into subspaces, which are then quantified. At 916, the genetic algorithm is used to link level of glycated hemoglobin or other blood constituents to various features.

With regard to the operational flow FIG. 9, cloud based image analysis software can be used to compute levels of blood glucose and glycated hemoglobin based on the high resolution (15 to 120 frames per second) perfusion video. In other implementations, image analysis may be performed locally on, e.g. a smartphone.

The present disclosure may be used to monitor and record short- and long-term changes in glucose and glycated hemoglobin levels respectively in an individual over a period of time. This is not limited to other blood constituents of interest that can be linked with retrospective data to specific conditions, outcomes or pathology correlations that can be made between the data received from the individual during the test and a database of blood constituent data characteristics for diseases. When the comparison is made, the correlations between characteristics of the light-based tissue perfusion patterns for an individual and the characteristics for a particular condition or disease can be used to give an indication of a pathological state. Appropriate therapies and dietary changes can be given to that individual and immediate feedback can be provided to observe the outcome and track the trajectory of the pathology with time. An untrained person can take frequent blood constituents measurements with a smart device such as a smart phone/watch, without requiring frequent skin punctures, blood handling nor a specialized medical device. The information can be analyzed by cloud software and the results transmitted to the mobile phone and presented to the user almost in real time. Additional software can used to recommend dietary changes or medications in order to maintain healthy levels, such as glucose levels. The information can be transmitted to a medical center, and a warning can be triggered if there are any risks.

In another embodiment, external light sources can be used to illuminate the appendage. Various semiconductor lasers could be integrated into an external ring (701) to provide specific wavelengths to correlate light transmittance, absorption and scattering of different blood and tissue constituent analysis.

It will be appreciated that the embodiments described above are given by way of example only and are not intended to limit the invention, the scope of which is determined by the attached claims. It is to be understood that the features described in one embodiment of the disclosure can be used either individually or collectively in other embodiments of the disclosure.

What is claimed is:

1. A method of performing blood constituent analysis, comprising:
    receiving a series of captured images that contain a digital signature of absorbed, transmitted and scattered light from a soft tissue appendage;
    determining a power spectral density (PSD) time series data from the digital signature;
    performing a model-based analysis to transform the PSD time series data to a noiseless model;
    applying a genetic algorithm to the noiseless model to estimate a level of blood constituent as a function of features that are extracted from a database of perfusion videos having associated blood panels; and
    communicating the level of blood constituent in a format suitable for display.

2. The method of claim 1, further comprising:
    converting the series of captured images to CMOS sectors; and
    placing the CMOS sectors into a scatter matrix, an absorption matrix, and a transmittance matrix.

3. The method of claim 1, wherein the model-based analysis uses a modified matching pursuit (MMP) algorithm.

4. The method of claim 1, further comprising:
    determining Red-Green-Blue (RGB) values from the PSD time series data in accordance with the relationships:

$$R = \int_0^\infty d\lambda (T_R(\lambda) I(\lambda))$$

$$G = \int_0^\infty d\lambda (T_G(\lambda) I(\lambda))$$

$$B = \int_0^\infty d\lambda (T_B(\lambda) I(\lambda));$$

reconstructing an approximated PSD by forming an invertible system of equations from the relationships; and
    estimating the level of blood constituent using the approximated PSD.

5. The method of claim 1, further comprising:
    recording changes in the level of blood constituent over time; and
    providing an indication of a pathological state of a subject based at least in part upon the blood constituent level changes.

6. A system for performing light-based tissue perfusion blood constituent analysis, comprising:
    a capture device that captures a series of images that contain a digital signature of absorbed, transmitted and scattered light from a soft tissue appendage;
    a processor that:
    receives the series of images and determines power spectral density (PSD) time series data from the digital signature;
    performs a model-based analysis to transform the PSD time series data to a noiseless model;
    applies a genetic algorithm to the noiseless model to estimate a level of blood constituent as a function of features that are extracted from a database of perfusion videos having associated blood panels; and
    a display that displays the level of blood constituent.

7. The system of claim 6, wherein the processor converts the series of captured images data to CMOS sectors, and places the CMOS sectors into a scatter matrix, an absorption matrix, and a transmittance matrix.

8. The system of claim 6, wherein the capture device includes a light source that is disposed adjacent to an objective lens of the capture device, the light source transmitting a plurality of wavelengths to enhance the absorption, scattering and transmittance patterns of a blood constituent of interest.

9. The system of claim 6, wherein capturing the digital signature of absorbed, transmitted and scattered light is performed using a series of CMOS images collected at 15 to 120 frames per second.

10. The system of claim 6, wherein the processing unit further:
    determines Red-Green-Blue (RGB) values from the PSD time series data in accordance with the relationships:

$$R = \int_0^\infty d\lambda (T_R(\lambda) I(\lambda))$$

$$G = \int_0^\infty d\lambda(T_G(\lambda)I(\lambda))$$

$$B = \int_0^\infty d\lambda(T_B(\lambda)I(\lambda));$$

reconstructs an approximated PSD by forming an invertible system of equations from the relationships; and
estimates the level of blood constituent using the approximated PSD.

11. The system of claim 6, wherein changes in the level of blood constituent are recorded over time, and wherein an indication of a pathological state of a subject is provided at least in part upon the blood constituent level changes.

12. A method for estimating blood constituent analysis, comprising:
capturing a series of images using a mobile device having a camera that includes a digital signature of absorbed, transmitted and scattered light from a soft tissue appendage;
obtaining a power spectral density (PSD) time series data from the series of images;
performing a model-based analysis to transform the PSD time series data to a noiseless model;
applying a genetic algorithm to the noiseless model to estimate a level of blood constituent as a function of features that are extracted from a database of perfusion videos having associated blood panels; and
presenting the level of blood constituent in a display of the mobile device.

13. The method of claim 12, further comprising:
converting the series of captured images to CMOS sectors; and
placing the CMOS sectors into a scatter matrix, an absorption matrix, and a transmittance matrix.

14. The method of claim 12, further comprising illuminating the soft tissue appendage using a light source that is disposed adjacent to an objective lens of the camera, the light source transmitting a plurality of wavelengths to enhance the absorption, scattering and transmittance patterns of a blood constituent of interest.

15. The method of claim 14, wherein the light source is an LED or a laser diode.

16. The method of claim 12, wherein the model-based analysis uses a modified matching pursuit (MMP) algorithm.

17. The method of claim 12, further comprising capturing the digital signature of absorbed, transmitted and scattered light using a series of CMOS images collected at 15 to 120 frames per second.

18. The method of claim 12, further comprising:
determining Red-Green-Blue (RGB) values from the PSD time series data in accordance with the relationships:

$$R = \int_0^\infty d\lambda(T_R(\lambda)I(\lambda))$$

$$G = \int_0^\infty d\lambda(T_G(\lambda)I(\lambda))$$

$$B = \int_0^\infty d\lambda(T_B(\lambda)I(\lambda));$$

reconstructing an approximated PSD by forming an invertible system of equations from the relationships; and
estimating the level of blood constituent using the approximated PSD.

19. The method of claim 12, further comprising:
recording changes in the level of blood constituent over time; and
providing an indication of a pathological state of a subject based at least in part upon the blood constituent level changes.

20. A device, comprising:
a memory that stores computer readable instructions;
a camera that includes a complementary metal-oxide semiconductor (CMOS) sensor; and one or more processors coupled to the memory, the one or more processors executing the computer-readable instructions to:
capture, using the camera, a series of images having a digital signature of absorbed, transmitted and scattered light from a soft tissue appendage;
obtain power spectral density (PSD) time series data from the series of images;
perform a model-based analysis to transform the PSD time series data to a noiseless model;
apply a genetic algorithm to the noiseless model to estimate a level of blood constituent as a function of features that are extracted from a database of perfusion videos having associated blood panels; and
present the level of blood constituent in a display of the device.

21. The device of claim 20, wherein the device further comprises a light source that is disposed adjacent to an objective lens of the camera, the light source transmitting a plurality of wavelengths to enhance the absorption, scattering and transmittance patterns of a blood constituent of interest.

22. The device of claim 20, wherein the digital signature of absorbed, transmitted and scattered light is captured by using a digital video made up of a series CMOS images collected at 15 to 120 frames per second.

23. The device of claim 20, wherein the one or more processors determine Red-Green-Blue (RGB) values from the PSD time series data in accordance with the relationships:

$$R = \int_0^\infty d\lambda(T_R(\lambda)I(\lambda))$$

$$G = \int_0^\infty d\lambda(T_G(\lambda)I(\lambda))$$

$$B = \int_0^\infty d\lambda(T_B(\lambda)I(\lambda)),$$

wherein the one or more processors reconstructs an approximated PSD by forming an invertible system of equations from the relationships, and
wherein the one or more processors estimate the level of blood constituent using the approximated PSD.

24. The device of claim 20, wherein the device records changes in the level of blood constituent over time, and wherein the device provides an indication of a pathological state of a subject based at least in part upon the blood constituent level changes.

25. The device of claim 20, wherein the device is a smartphone.

* * * * *